(12) United States Patent
Riley

(10) Patent No.: US 6,602,526 B2
(45) Date of Patent: Aug. 5, 2003

(54) ORAL COMPOSITIONS CONTAINING LOTUS

(75) Inventor: Patricia A. Riley, Golden Beach, FL (US)

(73) Assignee: Medical Doctors Research Institute, Sunrise, FL (US)

(*) Notice: Subject to any disclaimer, the term of this patent is extended or adjusted under 35 U.S.C. 154(b) by 70 days.

(21) Appl. No.: 10/041,313

(22) Filed: Jan. 7, 2002

(65) Prior Publication Data
US 2002/0098253 A1 Jul. 25, 2002

Related U.S. Application Data

(63) Continuation-in-part of application No. 09/953,309, filed on Sep. 14, 2001, which is a continuation-in-part of application No. 09/327,927, filed on Jun. 8, 1999, now abandoned, which is a continuation-in-part of application No. 08/804,532, filed on Feb. 21, 1997, now abandoned.
(60) Provisional application No. 60/012,158, filed on Feb. 23, 1996.

(51) Int. Cl.$^7$ ............................................. A61K 35/78
(52) U.S. Cl. ...................... 424/776; 424/94.5; 424/725; 424/773; 424/774; 424/779
(58) Field of Search ............................ 424/94.5, 725, 424/773, 774, 776, 779

(56) References Cited

U.S. PATENT DOCUMENTS

| | | | |
|---|---|---|---|
| 367,337 A | 7/1887 | Carson | 424/725 |
| RE33,993 E | 7/1992 | Grollier et al. | 424/74 |
| 5,190,762 A | 3/1993 | Yarosh | 424/450 |
| 5,272,079 A | 12/1993 | Yarosh | 435/193 |
| 5,296,231 A | 3/1994 | Yarosh | 340/2.22 |
| 5,925,348 A | 7/1999 | Riley et al. | 424/94.5 |
| 5,948,443 A | 9/1999 | Riley et al. | 424/643 |
| 5,976,568 A | 11/1999 | Riley | 424/451 |

FOREIGN PATENT DOCUMENTS

| | | |
|---|---|---|
| JP | 1090129 | 4/1986 |
| JP | 3190809 | 8/1991 |
| JP | 4247012 | 9/1992 |
| JP | 11071234 | 3/1999 |

OTHER PUBLICATIONS

Onishi et al., Chem. Pharm. Bull (Tokyo) 32(2): 646–650 (1984). Abstract.*
Lotus L., Illustrated Flora of the Northeastern United States and Adjacent Canada, (2) 398, 1963.
MacLaren et al. Expression and Purification of a Human Recombinant Methyltransferase That Repairs Damaged Proteins, Protein Expression and Purification (6) 99–108 (1995).
Mukherjee et al. Antidiarrhoeal Evaluation of Nelumbo Nucifera Rhizome Extract, Indian Journal of Pharmacology (27) 262–264 (1995).
Shen–Miller et al. Exceptional Seed Longevity and Robust Growth: Ancient Sacred Lotus from China, American Journal of Botany (11) 1367–1380 (1995).

* cited by examiner

Primary Examiner—Jean C. Witz
(74) Attorney, Agent, or Firm—Robert E. Pershes

(57) ABSTRACT

Oral compositions of extract of the Lotus (Nelumbo) as an active anti-aging agent in a suitable carrier or vehicle, along with methods of treatment to reduce signs of aging such loss of elasticity, age spots, blemishes, enlarged pores, fine lines, wrinkles, and to promote overall younger looking skin by using said compositions. This composition also reverses signs of aging in the body by improving general overall well-being, stamina, sexual function, memory, circulation, vision, hair and nail growth, sleep, muscle tone, lipolysis and overall health, making the person feel and look younger.

20 Claims, 1 Drawing Sheet

ORAL COMPOSITIONS CONTAINING LOTUS

This application is a continuation-in-part of U.S. patent application Ser. No. 09/953,309, filed Sep. 14, 2001, currently pending, which is a continuation-in-part of U.S. patent application Ser. No. 09/327,927, filed Jun. 8, 1999, now abandoned, which is a continuation-in-part of U.S. patent application Ser. No. 08/804,532, filed Feb. 21, 1997, now abandoned, which is a continuation-in-part of U.S. provisional patent application 60/012,158, filed Feb. 23, 1996, now abandoned.

FIELD OF THE INVENTION

The present invention relates to the use of lotus in dietary compositions for combating aging and its symptoms and methods for treatment and prevention of aging and its symptoms using such compositions. The dietary compositions may use, in combination or alone, Sacred Lotus seed extract, ground Sacred Lotus seeds, other Lotus varieties or parts of the Lotus. The present invention also concerns the use of components of the lotus plant, such as methyltransferase and especially L-isoaspartyl methyltransferase, ascorbic acid, gluthathione, and dopamine agonists present within the plant, and any locations of the lotus plant in which these components may be found, including the seed, fruit, husk, pithe, shell, plumule, petals, pastures, stalks, leaves, roots, stems, pollen, carpels, ovals, rhizomes, peltates and stipules, which may be classified with other names.

BACKGROUND

Within the dermis are highly stable fibers of collagen and elastin. Collagen, the most abundant protein in the body, has a high tensile strength thus preventing skin from being torn by over stretching. Elastin, also a protein, allows movement. As skin ages, elastic tissue increases but it loses the ability to stretch and recover. This loss of resiliency and elasticity is accompanied by increased stiffness, sagging and wrinkling. Changes in collagen solubility and cross-linking contribute to loss of elasticity.

On the cellular level, aspartyl and asparaginyl residues are prominent at sites of age-related damage in proteins. These damaged sites have been characterized in a variety of proteins, but are particularly common in the long-lived proteins. Enzymatic mechanisms for reversing damage to DNA are well established and have been shown to be essential for extended lifespan.

Experiments performed in vitro with recombinant and chemically modified polypeptides have shown that the presence of an L-isoaspartyl residue may alter both enzymatic activity and the binding of other molecules.

Limiting the accumulation of these residues within cells is currently believed to be important; all human cells examined thus far contain an L-isoaspartyl/D-aspartyl protein methyltransferase that has been proposed to serve this function. It is also believed that this methyltransferase can recognize both D-aspartyl and L-isoaspartyl residues. In addition, it is thought that this enzyme may have the ability to reverse at least part of the damage to protein molecules.

Although the human isoaspartyl protein repair methyltransferase has been purified from red blood cells and had its protein sequence determined, in addition to harvesting a variant in a bacterial system, the availability and use of methyltransferase has been limited.

On or around Nov. 14, 1995, however, it was reported that scientists germinated a 1,288 year old Sacred Lotus seed. The research, reported in the November issue of the American Journal of Botany, began in 1982, when Jane Shen-Miller, a plant physiologist at the University of California at Los Angeles (UCLA), obtained seven brown, oval-shaped Sacred Lotus seeds from the Beijing Institute of Botany.

In 1983, Jane Shen-Miller filed through the hard shells of four of the ancient Sacred Lotus seeds and watched three of them sprout. She then dried and burned the seedlings so she could use radiocarbon dating to establish the ages, the oldest of which was 1,288 years old.

According to the November 1995 report, one of those Sacred Lotus seeds had been in the ground for over 1,200 years; it therefore has been postulated that the Sacred Lotus seeds act as embryos that possess anti-aging properties. Up until this point, geneticists knew only about proteins that repaired damaged DNA. But findings have suggested that the L-isoaspartyl methyltransferase (MT) enzyme, found in the Sacred Lotus seeds and nearly all other organisms, may have the ability to repair other proteins—those that make up cells and tissues, thus slowing tissue decay, and reversing some aspects of aging.

In these ancient Sacred Lotus seeds, the MT enzyme was present at levels comparable to modem day Sacred Lotus seeds. Damaged proteins did not accumulate within the ancient Sacred Lotus seeds, suggesting that the MT enzyme, possibly along with other constituents, kept the ancient Sacred Lotus seeds alive for so many years.

Before U.S. Pat. No. 5,925,348 (Riley et al.), it was unknown as to whether use of methyltransferase, or extracts or components of the Sacred Lotus plant, or extracts or components of other varieties of the Lotus plant (genus Nelumbo) in oral compositions would be effective in combating signs of aging, repairing damaged skin and/or restoring skin to a more youthful appearance. Moreover, there were no known acceptable products available which incorporated methyltransferase, extracts or components of the Sacred Lotus, or extracts or components of other varieties of the Lotus plant (genus Nelumbo) for combating aging, repairing damaged skin and/or restoring skin to a more youthful appearance.

Since filing the patent application for U.S. Pat. No. 5,925,348 (Riley et al.), we have discovered that our clients who utilize oral compositions containing methyltransferase, extracts or components of the Sacred Lotus, or extracts or components of other varieties of the Lotus plant (genus Nelumbo) have experienced not only improved skin quality, but other categories of improvement as well, which indicate reversal of the aging process. Included in these categories are improved stamina, sexual function, memory retention, circulation, vision and hair and nail growth. It is theorized that methyltransferase, or some other as yet undetermined component of lotus, enhances natural repair by limiting the accumulation of aspartyl and asparaginyl residues at the cellular level and hindering age-related damage in proteins.

In addition, some varieties of Lotus, such as Blue Lotus, have been shown to contain dopamine agonists. This chemical constituent could possibly assist in the release of growth hormone, a vital hormone that declines with age. Replacement of this hormone has been shown to reverse signs of aging and increase skin thickness, decrease wrinkles, improve bone density, improve muscle tone, and lipolyses, favoring a more youthful body composition.

Consequently, there exists a need for acceptable delivery systems that incorporate methyltransferase, dopamine agonists, or extracts or components of the Sacred Lotus plant for preventing and reversing signs of aging, repairing damaged tissue of the body's organs, the largest being the skin, and restoring skin to a more youthful appearance as well as restoring overall good health. It is further theorized that other species in the Nelumbo family will have similar beneficial effects because of similar chemical constituents.

SUMMARY OF THE INVENTION

The present invention alleviates and overcomes certain of the above-mentioned problems and shortcomings of the present state of the art through the discovery of novel acceptable oral delivery systems which embody methyltransferase, extracts or components of the Sacred Lotus plant, or extracts or components of other varieties of the Lotus plant (genus Nelumbo) for effectively treating and preventing aging, repairing damaged skin and restoring skin to a more youthful appearance and methods of using same.

Accordingly, it is the object of the invention to provide a general method for prevention or alleviation of age-related damage to the skin and associated decline of body function and appearance from aging through the oral use of extracts of the lotus or its components, such as methyltransferase, in combination with a suitable carrier or vehicle.

Another object is to have the person taking the supplement to experience improvement in physical attributes helping the person to:

feel younger and look younger have increased stamina have increased sexual function have improved circulation have improved hair and nail strength and growth have improved vision have improved mental focus, performance and memory have improved overall health have improved immunity function have improved body composition, with greater muscle tone have improved body composition, with less body fat have improved ability to sleep have improved vitality have improved energy have improved mood restore his or her skin to a more youthful appearance improve the vibrancy of his or her skin improve the smoothness of his or her skin improve the tone of his or her skin improve the elasticity of his or her skin have less the appearance of wrinkles Another object is to use the extract or ground seeds of the Sacred Lotus (*Nelumbo nucifera*) as a natural source of methyltransferase. It has now been observed, surprisingly and unexpectedly, that by using an extract or ground seeds of the Sacred Lotus by oral administration as an active agent, signs of aging can be reduced, or even reversed.

Also, until U.S. Pat. No. 5,925,348 and the present invention, there were no acceptable vehicles utilizing lotus flowers and seeds and its other natural components, such as methyltransferase, in a dietary formulation. Thus, another object of the present invention is formulations of Lotus seed in dietary supplements to improve the youthful appearance of the skin, repair visible damage, and reduce general signs of aging including loss of elasticity, fine lines, wrinkles, loss of vitality, reduced muscle tone, decreased sexual function, reduced mental performance, to promote the sense of feeling younger with improved general overall good health.

Another object is the formulation of dietary supplements providing anti-aging benefits from methyltransferase found in the Sacred Lotus seeds and other varieties of Lotus.

Another object of the invention is to formulate dietary supplements using other parts of the plant or extracts of other parts for antiaging.

Another object of the invention is to formulate dietary supplements using other varieties of the Lotus family, such as Blue Lotus, Yellow Lotus, White Lotus, and so forth, with different parts and extracts of these parts.

A suitable carrier or vehicle will include the formulation of powders, tablets, gelcaps, food additives, drops, liquids, beverages, pills, capsules, lozenges, and pastes comprised of Lotus or its components.

These and other objectives are achieved by the present invention which is directed to an oral formulation for the protection of the body, especially its largest organ, the skin, against damage caused by aging and a method for preventing or alleviating such damage and restoring the whole body to a more youthful appearance and vitality level by employing such in an oral formulation.

The formulation is a suitable orally acceptable, non-toxic, non-allergenic carrier containing Sacred Lotus plant and/or other Lotus plants and/or its chemical constituents, such as methyltransferase and other components of the seed.

The above features and advantages of the present invention will be better understood with reference to the accompanying tables, figure, detailed description and examples. It should also be understood that the particular methods and formulations illustrating the present invention are exemplary only and not to be regarded as limitations on the present invention.

DETAILED DESCRIPTION

Figure 1:
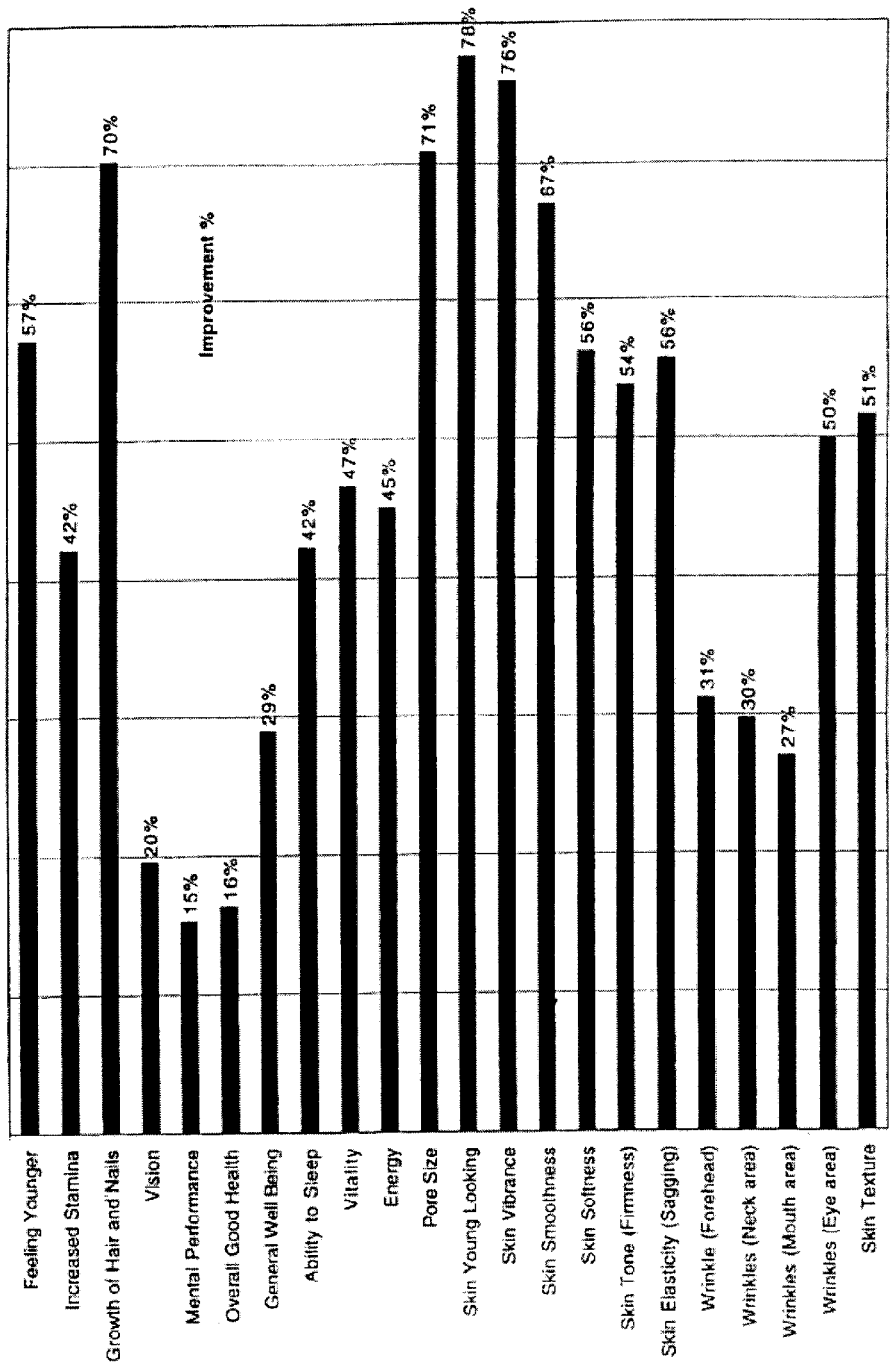
FIG. 1 provides a graphical representation of the results of dietary supplementation of Sacred Lotus seed upon the skin and physical and mental assessments.

By way of illustrating and providing a more complete appreciation of the present invention and many of the attendant advantages thereof, the following detailed description and examples are given concerning the novel oral delivery system which embody methyltransferase or extracts or components of the Sacred Lotus plant or other varieties of Lotus plants for effectively treating and preventing aging, repairing damaged skin, restoring skin to a more youthful appearance, improving overall health and methods of using same.

The present invention uses Sacred Lotus seed and other extracts of Lotus plants in dietary formulas to combat aging. It is believed that the use of Sacred Lotus seeds in dietary supplements accomplishes anti-aging effects based on anti-aging factors (enzymes such as methyltransferase and growth hormone agonists) which are present in the seeds.

Moreover, Sacred Lotus seeds contain certain antioxidants such as vitamin C and glutathione which may contribute to anti-aging effects on skin and in the body and may even contain other beneficial factors.

In accordance with the present invention, methyltransferase and/or the natural compounds found in an extract of Sacred Lotus seeds may be used in an effort to repair age-related signs in the body and skin such as lines, wrinkles, and/or loss of elasticity, as well as revitalize overall general health. Other sources of methyltransferase that may be used in the invention are components of Sacred Lotus plants, extracts of Yellow Lotus seeds or components of Yellow Lotus plants, extracts of Red Lotus seeds or components of Red Lotus plants, extracts of Purple Lotus seeds or components of Purple Lotus plants, extracts of Pink Lotus seeds or components of Pink Lotus plants, extracts of White Lotus seeds or components of White Lotus plants, extracts of Blue Lotus seeds or components of Blue Lotus plants, extracts of Golden Lotus seeds or components of Golden Lotus plants, extracts of Orange Lotus seeds or components of Orange Lotus plants, and extracts of Egyptian Lotus seeds or components of Egyptian Lotus plants, or other Lotus seeds or components of other Lotus plants in which methyltransferase may be present. In addition to extracts from the seeds, methyltransferase may also be extracted from the lotus fruit, husk, pithe, shell, plumule, petals, stalks, pastures, leaves, roots, stems, pollen, carpels, ovals, rhizomes, peltates, and stipules.

An extract is prepared, for example, as follows. Maceration is the preferred process since no heat is used which may destroy or alter temperature-sensitive components; however percolation, digestion, infusion, and decoction are within the scope of the invention as more scientific information becomes available.

A twenty percent extract of Nelumbo nucifera is generally used and prepared by placing 200 grams of finely milled untreated whole seeds, including husks and pithes, in a stoppered container with about 750 mL of a 50/50 wt/wt mixture of Purified Water and Propylene Glycol, USP, and allowed to stand for a period of at least 3 days in a warm place with frequent agitation, until soluble matter is dissolved. The mixture is filtered and, after most of the liquid has drained, the residue on the filter is washed with sufficient quantity of the solvent mixture; the filtrates are combined to produce 1000 mL.

It is also within the scope of the present invention to use different amounts of the seed, other parts of the plant as well as other species, solvents and mixtures.

While it is believed that Sacred Lotus, *Nelumbo nucifera*, is a preferred species and the seed is the preferred part, other parts of the plant or other species, such as the Yellow Lotus, *Nelumbo Lutea*, Blue Lotus, *Nelumbo Caerulea*, containing these "anti-aging" enzymes or constituents are believed to be suitable alternatives for accomplishing the objectives of the present invention. Other species include Yellow Lotus, *Nelumbo lutea*, Red Lotus, Purple Lotus, Pink Lotus, White Lotus, Blue Lotus, *Nelumbo caerulea*, Golden Lotus, Orange Lotus and Egyptian Lotus. Other parts of the plant include husk, fruit, pithe, shell, plumule, petals, pastures, stalks, leaves, roots, stems, pollen, carpels, ovals, rhizomes, peltates, and stipules.

A composition according to the present invention for oral administration contains an effective amount of the anti-aging agent Sacred Lotus seed (with husk, shell and plumele) from 0.01% to 99.9% by weight of the ground seed or 0.05% to 99.9% by weight of the extract relative to the total weight of the composition. More particularly, and by way of example, an oral composition containing ground Sacred Lotus seed may be prepared as follows. The whole Sacred Lotus seed with husk, shell and plumele (pithe or embryo), supplied by W.T.H., 130 Wing Lok St., 8/F, Hong Kong, is first ground through a coffee mill having a fine screen (#24 mesh or 700 micron particle size). The ground seeds may then be powder blended with other selected components to formulate oral delivery systems in accordance with the present invention, as discussed in greater detail hereinafter.

An oral composition according to the present invention may be in any of the dosage forms which are generally used for dietary supplements such as liquids, gels, powders, tablets, caplets, capsules, gelcaps, food additives, drops, beverages, pills, lozenges, rinses, pastes, gums and soft gels. While it is generally preferable to formulate the oral dosages to each contain, for example from about 350 mcg to 500 mcg of Sacred Lotus seed for administration twice daily, it should be understood that any effective dosage strength may be formulated for administration at any effective daily interval, so long as the objectives of the instant invention are not defeated.

Compositions of the present invention may also contain additives, such as water, alcohols, oils (mineral, vegetable, animal and synthetics), glycols, colorants, preservatives, emulsifiers, gelling agents, gums, esters, hormones, steroids, anti-oxidants, silicones, polymers, fragrances, flavors, sunscreens, other active ingredients, acids, bases, buffers, vitamins, minerals, salts, polyols, proteins and their derivatives, essential oils, other enzymes, co-enzymes and extracts, surfactants, detergents, soaps, anionics, non-ionics, ionics, waxes, lipids, UV filters, stabilizers, fillers, celluloses, glycans, amines, solubilizers, thickeners, sugars and sugar derivatives, ceramides, sweeteners and the like, so long as such additives do not defeat the objectives of the present invention.

A composition according to the present invention as an effective anti-aging agent may be employed alone, that is without the use of additional actives, or the Sacred Lotus seed may be used to enhance other ingredients. Moreover, it should be understood by those versed in this art that the present invention contemplates treating the skin with either the oral compositions of this invention alone or concomitantly administering the topical compositions such as described in U.S. Pat. No. 5,925,348 for enhanced benefits. It is believed that when both the oral composition of the present invention and topical routes are administered, such combination therapy will promote both good health and radiant skin, especially when the oral compositions include micronutrients, such as in the oral composition set forth in Examples hereinafter.

One preferred composition combines the Sacred Lotus seed with glucosamine and cysteine for their role in glycosaminoglycan (a protein-sugar complex essential for normal hydration in the skin) synthesis plus antioxidants such as vitamins A, C, E and extracts of grape seed and green tea, to protect the skin from free radicals and alleviate further cellular damage.

Other items such as lecithin, squalene, panthenol, vitamin D3, jojoba oil, olive oil, glycerin and other moisturizers also appear to benefit with the addition of Sacred Lotus seed in providing moisture into the skin, enhancing its repair process, promoting elasticity and making the skin appear younger.

Hydroquinone, sulfur and salicylic acid also appear to exhibit synergism with Sacred Lotus seed extract.

The following examples are given for illustrative purposes only to delineate some of the features of the invention and are not intended to be limiting. As to exemplary formulations set forth below, the quantities are given in percent by approximate weight (mg) or approximate units (IU) unless otherwise noted based on recommended dosage.

EXAMPLE 1

In order to test the effectiveness of the oral administration of Sacred Lotus extract on the skin of a human, Sacred Lotus Seed Daily Nutrients, as set forth below, with instructions for use, were given to a group of nine healthy volunteers for 60 days. The group was supervised by a technician skilled in dietary supplements. All the volunteers in the group were instructed not to use any other vitamin product during that period and they were given a two-page questionnaire to complete. Page 1 reflected the condition of their skin at the start of the study and after 60 days of taking the Sacred Lotus Seed Daily Nutrients. On the second page, they indicated physical and mental conditions, which they experienced in the areas of energy, vitality, ability to sleep, etc. These experimental results are reported in Tables 1, 2, 3 & 4 and tabulated in Tables 5 & 6.

Tables 5 and 6 show that dramatic improvements occurred in all categories, especially in Younger Looking Skin (78%), Skin Vibrancy (76%), Pore Size Improvement (71%), Growth of Hair and Nails (70%), Skin Smoothness (67%), Feeling Younger (57%), Skin Elasticity (56%), Skin Softness (56%), and Skin Tone (54%). FIG. 1 displays a graphical representation of the results of dietary supplementation of Sacred Lotus seed upon the skin and physical and mental assessments.

As demonstrated in Tables 1 through 6 and FIG. 1, the use of Sacred Lotus Seed in dietary supplements provides anti-aging effects due to anti-aging factors (enzymes such as methyltransferase), which is present in the seed. In addition, Sacred Lotus seeds contain certain antioxidants, such as Vitamin C and glutathione, which also may play a role in anti-aging.

| Sacred Lotus Seed Daily Nutrients | |
|---|---|
| Vitamin A Palmitate | 1750 IU |
| Natural Beta Carotene | 750 IU |
| Lycopene | 0.375 mg |
| Lutein | 0.375 mg |
| Vitamin E (d-alpha tocopheryl acetate and mixed tocopherols) | 50 IU |
| Cholecalciferol (Vitamin D3) | 200 IU |
| Vitamin C | 150 mg |
| Thiamine HCl | 4 mg |
| Riboflavin | 5 mg |
| Niacinamide | 20 mg |
| Pyridoxine HCl | 6 mg |
| Folic Acid | 200 mcg |
| Vitamin B-12 | 5 mcg |
| Pantothenic Acid | 7.5 mg |
| Biotin | 75 mcg |
| Calcium (Carbonate & Citrate) | 12.5 mg |
| Magnesium Oxide | 18.75 mg |
| Iron (Fumarate) | 7.5 mg |
| Zinc (Sulfate & Gluconate) | 7.5 mg |
| Manganese Gluconate | 2 mg |
| Selenium (L-Selenomethionine & Citrate) | 35 mcg |
| Chromium Nicotinate | 37.5 mcg |
| Copper Gluconate | 0.5 mg |
| Green Tea Extract | 7.5 mg |
| Grape Seed Extract | 7.5 mg |
| N-Acetyl Glucosamine | 15 mg |
| Citrus Bioflavanoids | 37.5 mg |
| N-Acetyl Cysteine | 5 mg |
| Sacred Lotus seed extract | 350 mcg |
| Magnesium Stearate (lubricant) | 8.4 mg |
| Stearic Acid (binder) | 42 mg |
| Microcrystalline Cellulose (tablet aide) qs | 840 mg |

Procedure:

All of the above were mixed in a powder blender until completely homogenous. The mixed powder was fed into a tablet press and compressed into tablets.

A unique blend of protective antioxidants and essential nutrients with the entire Sacred Lotus seed (in food preparations the pithe (embryo) or plumule is removed due to bitter taste) used to promote good health, vitality and radiant skin. This product may be taken, for example, twice per day, i.e., take one tablet with breakfast and one tablet with lunch or dinner.

EXAMPLE 2

In order to further utilize the anti-aging factors present in the Sacred Lotus seeds and its compatibility with other ingredients, a Longevity Antioxidant supplement was formulated. The basic rationale is that by augmenting cell defenses against free radicals, risk factors for major diseases, such as cancer and heart disease are reduced, increasing one's life-span through better health.

This composition combines Sacred Lotus seeds with additional antioxidants, such as Vitamin E, Green Tea Leaf extract (which contains polyphenols), Grape Seed extract, Co-Enzyme Q10, Lycopene and Pycnogenol (Pine Bark extract) to help prevent oxidative damage; Broccoli Sprouts and Citrus Bioflavonoids for cancer prevention; Grape Skin and Olive Leaf extracts to reduce the risk of heart disease. The antioxidants Co-Enzyme Q10 and Quercetin are also beneficial for a healthy heart. Ginkgo Biloba was added for a clear alert mind; Bilberry for healthy vision and Ginseng for added vitality.

| Longevity Antioxidants | |
|---|---|
| Natural Vitamin E | 8 IU |
| Broccoli Whole Plant | 320 mg |
| Citrus Fruit Bioflavonoids Complex | 160 mg |
| Rose Hips | 40 mg |
| Alpha Lipoic Acid | 24 mg |
| Bilberry Extract | 24 mg |
| Olive Leaf Extract | 24 mg |
| Green Tea Leaf Extract | 24 mg |
| Calcium D-Glucarate | 20 mg |
| N-Acetyl Cysteine | 20 mg |
| Grape Seed Extract | 20 mg |
| Grape Leaf Extract | 20 mg |
| L-Carnosine | 16 mg |
| Quercetin Dihydrate | 16 mg |
| Chinese Ginseng | 12 mg |
| L-Carnitine (L-Tartrate) | 8 mg |
| Ginkgo Biloba Leaf Extract | 8 mg |
| Silymarin (From Milk Thistle Extract) | 8 mg |
| CoEnzyme Q10 (Ubiquinone) | 8 mg |
| Wheat Sprout Complex | 8 mg |
| Tumeric Root Extract | 4 mg |
| Lycopene | 0.08 mg |
| Lutein | 0.08 mg |
| Natural Vanillin | 800 mcg |
| Pycnogenol (Pine Bark Extract) | 800 mcg |
| Sacred Lotus Seed Extract | 800 mcg |
| Magnesium Stearate (lubricant) | 9 mg |
| Stearic Acid (Binder) | 50 mg |
| Microcrystalline Cellulose (tableting aid) qs | 1200 mg |

Procedure:

All of the above were mixed in a powder blender until completely homogenous. The mixed powder was fed into a tablet press and compressed into tablets.

EXAMPLE 3

Daily Nutrient Supplements were designed to give a precise amount of vitamins, minerals and trace elements essential to good health and radiant skin. The formula is a nutritional system that provides morning, mineral and evening complex for increased absorption, due to the pres ence of more fat-soluble nutrients in the evening, when more fats are present in the diet.

| Morning Nutrients | |
|---|---|
| Vitamin C | 120 mg |
| Thiamine HCl | 5 mg |
| Riboflavin | 5.66 mg |
| Niacinamide | 30 mg |
| Pyridoxine HCl | 6 mg |
| Folic Acid | 400 mcg |
| Vitamin B-12 | 12 mcg |
| Biotin | 300 mcg |
| Pantothenic Acid | 10 mg |
| Calcium (Citrate and Ascorbate) | 150 mg |
| Iron (Fumerate) | 12 mg |
| Copper (Gluconate) | 0.75 mg |
| Manganese (Gluconate) | 3 mg |
| Chromium (Polynicotinate) | 100 mcg |
| Grape Seed Extract | 10 mg |
| Grape Skin Extract | 10 mg |
| Sacred Lotus Seed | 10 mg |
| Green Tea Leaf Extract | 10 mg |
| Magnesium Stearate (lubricant) | 9 mg |
| Stearic Acid (binder) | 50 mg |
| Microcrystalline Cellulose (tableting aid) qs | 1200 mg |

Procedure:

All of the above were mixed in a powder blender until completely homogenous. The mixed powder was fed into a tablet press and compressed into tablets.

EXAMPLE 4

For the person who already has a preferred daily vitamin, 500 mg of ground blue lotus seed were placed in gelatin capsules. This enables the person to achieve the benefits of lotus supplementation, without having to switch vitamin formulations.

EXAMPLE 5

For the person who already has a preferred daily vitamin, 500 mg of ground sacred lotus seed were placed in gelatin capsules. This enables the person to achieve the benefits of lotus supplementation, without having to switch vitamin formulations.

In conclusion, the use of Sacred Lotus seeds in dietary supplements accomplishes anti-aging effects based on anti-aging factors (enzymes such as methyltransferase), which are present in the seeds. Also, Sacred Lotus seeds contain certain antioxidants such as Vitamin C and gluthathione, which may contribute to anti-aging effects on skin, along with methyltransferase and may even contain some other beneficial factors not yet discovered.

The present invention may, of course, be carried out in other specific ways than those herein set forth without departing from the spirit and essential character of the present invention. The present embodiments are, therefore, to be considered in all respects as illustrative and not restrictive and all changes coming within the meaning and equivalency range of the appended claims are intended to be embraced herein.

The Effectiveness of the Oral Administration of the Sacred Lotus (Methyltransferase) Upon the Skin of a Human

TABLE 1

Skin Condition before taking Lotus (Methyltransferase) Daily Nutrient Tablets

| Skin Condition | Score | | | | | | | | | Average |
|---|---|---|---|---|---|---|---|---|---|---|
| Skin Texture | 1 | 1 | 7 | 2 | 4 | 7 | 4 | 3 | 4 | 3.67 |
| Wrinkles (Eye area) | 1 | 2 | 4 | 2 | 5 | 6 | 2 | 2 | 2 | 2.89 |
| Wrinkles (Mouth area) | 1 | 2 | 4 | 2 | 5 | 7 | 1 | 1 | 3 | 2.89 |
| Wrinkles (Neck area) | 2 | 2 | 4 | 3 | 4 | 7 | 1 | 1 | 3 | 3.00 |
| Wrinkle (Forehead) | 1 | 4 | 5 | 2 | 5 | 7 | 3 | 3 | 2 | 3.56 |
| Skin Elasticity (Sagging) | 1 | 2 | 6 | 3 | 5 | 7 | 3 | 1 | 2 | 3.33 |
| Skin Tone (Firmness) | 1 | 2 | 7 | 2 | 4 | 7 | 2 | 1 | 2 | 3.11 |
| Skin Softness | 1 | 2 | 7 | 3 | 5 | 6 | 3 | 1 | 4 | 3.56 |
| Skin Smoothness | 1 | 2 | 6 | 2 | 5 | 6 | 3 | 1 | 4 | 3.33 |
| Skin Vibrance | 1 | 2 | 5 | 2 | 4 | 4 | 3 | 1 | 3 | 2.78 |
| Skin Young Looking | 1 | 2 | 6 | 2 | 5 | 6 | 2 | 1 | 2 | 3.00 |
| Pore Size | 1 | 2 | 7 | 4 | 3 | 3 | 1 | 2 | 1 | 2.67 |

Rating Scale
1 = very displeased, 2 = slightly displeased, 3 = fair, 4 = average, 5 = better than average, 6 = moderately pleased, 7 = pleased, 8 = very pleased.

TABLE 2

Skin Condition after taking Lotus (Methyltransferase) Daily Nutrient Tablets (60 days)

| Skin Condition | Score | | | | | | | | | Average |
|---|---|---|---|---|---|---|---|---|---|---|
| Skin Texture | 7 | 3 | 7 | 4 | 5 | 7 | 8 | 5 | 4 | 5.75 |
| Wrinkles (Eye area) | 8 | 4 | 5 | 4 | 6 | 3 | 2 | 4 | 3 | 4.50 |
| Wrinkles (Mouth area) | 1 | 4 | 4 | 3 | 6 | 8 | 1 | 3 | 3 | 3.75 |
| Wrinkles (Neck area) | 2 | 4 | 5 | 4 | 5 | 8 | 1 | 3 | 3 | 4.00 |
| Wrinkle (Forehead) | 1 | 6 | 5 | 6 | 6 | 8 | 3 | 4 | 3 | 4.88 |
| Skin Elasticity (Sagging) | 4 | 4 | 7 | 4 | 6 | 8 | 3 | 3 | 3 | 4.88 |
| Skin Tone (Firmness) | 7 | 4 | 7 | 4 | 5 | 8 | 2 | 3 | 3 | 5.00 |
| Skin Softness | 4 | 4 | 7 | 5 | 6 | 8 | 8 | 4 | 4 | 5.75 |
| Skin Smoothness | 4 | 4 | 7 | 5 | 6 | 8 | 8 | 4 | 4 | 5.75 |
| Skin Vibrance | 5 | 4 | 6 | 4 | 5 | 7 | 7 | 3 | 3 | 5.13 |
| Skin Young Looking | 5 | 4 | 6 | 5 | 7 | 8 | 7 | 3 | 3 | 5.63 |
| Pore Size | 4 | 4 | 7 | 5 | 5 | 3 | 8 | 3 | 2 | 4.88 |

Rating Scale
1 = very displeased, 2 = slightly displeased, 3 = fair, 4 = average, 5 = better than average, 6 = moderately pleased, 7 = pleased, 8 = very pleased.

The Effectiveness of the Oral Administration of the Sacred Lotus (Methyltransferase) Upon the Skin of a Human

TABLE 3

Physical/Mental Condition before taking Lotus (Methyltransferase) Daily Nutrient Tablets

| Physical/Mental Condition | Score | | | | | | | | | Average |
|---|---|---|---|---|---|---|---|---|---|---|
| Energy | 1 | 2 | 7 | 3 | 4 | 2 | 4 | 3 | 3 | 3.25 |
| Vitality | 1 | 2 | 6 | 3 | 5 | 2 | 3 | 3 | 3 | 3.13 |
| Ability to Sleep | 2 | 3 | 5 | 2 | 8 | 2 | 1 | 2 | 1 | 3.13 |
| General Well Being | 8 | 2 | 5 | 3 | 7 | 3 | 2 | 4 | 4 | 4.25 |

TABLE 3-continued

Physical/Mental Condition before taking Lotus (Methyltransferase) Daily Nutrient Tablets

| Physical/Mental Condition | | | Score | | | | | | | Average |
|---|---|---|---|---|---|---|---|---|---|---|
| Overall Good Health | 8 | 2 | 5 | 4 | 7 | 4 | 2 | 7 | 4 | 4.88 |
| Mental Performance | 8 | 2 | 6 | 4 | 7 | 7 | 2 | 6 | 4 | 5.25 |
| Vision | 2 | 2 | 7 | 3 | 3 | 7 | 2 | 6 | 4 | 4.00 |
| Growth of Hair and Nails | 8 | 1 | 7 | 2 | 3 | 1 | 1 | 3 | 4 | 3.25 |
| Increased Stamina | 2 | 2 | 6 | 2 | 6 | 4 | 2 | 3 | 4 | 3.38 |
| Feeling Younger | 2 | 2 | 4 | 2 | 4 | 6 | 2 | 3 | 3 | 3.13 |

Rating Scale
1 = very displeased, 2 = slightly displeased, 3 = fair, 4 = average, 5 = better than average, 6 = moderately pleased, 7 = pleased, 8 = very pleased.

TABLE 4

Physical/Mental Condition after taking Lotus (Methyltransferase) Daily Nutrient Tablets (60 days)

| Physical/Mental Condition | | | Score | | | | | | | Average |
|---|---|---|---|---|---|---|---|---|---|---|
| Energy | 5 | 4 | 7 | 5 | 7 | 6 | 1 | 4 | 3 | 4.88 |
| Vitality | 5 | 4 | 6 | 5 | 7 | 6 | 1 | 4 | 3 | 4.75 |
| Ability to Sleep | 4 | 3 | 6 | 4 | 8 | 5 | 1 | 5 | 1 | 4.50 |
| General Well Being | 8 | 5 | 6 | 5 | 8 | 6 | 2 | 5 | 4 | 5.63 |
| Overall Good Health | 8 | 5 | 5 | 4 | 8 | 6 | 2 | 8 | 4 | 5.75 |
| Mental Performance | 8 | 2 | 6 | 8 | 8 | 7 | 2 | 8 | 4 | 6.13 |
| Vision | 1 | 2 | 7 | 5 | 7 | 7 | 2 | 8 | 4 | 4.88 |
| Growth of Hair and Nails | 8 | 2 | 7 | 4 | 7 | 7 | 7 | 5 | 4 | 5.88 |
| Increased Stamina | 4 | 4 | 7 | 5 | 7 | 6 | 2 | 5 | 4 | 5.00 |
| Feeling Younger | 4 | 4 | 5 | 7 | 7 | 7 | 2 | 5 | 3 | 5.13 |

Rating Scale
1 = very displeased, 2 = slightly displeased, 3 = fair, 4 = average, 5 = better than average, 6 = moderately pleased, 7 = pleased, 8 = very pleased.

The Effectiveness of the Oral Administration of the Sacred Lotus (Methyltransferase) Upon the Skin of a Human

TABLE 5

Improvement Percentage of Skin Condition after taking Lotus (Methyltransferase) Daily Nutrient Tablets (60 days)

| Skin Condition | Average Score Before Treatment | Average Score After Treatment | Improvement | Increased % |
|---|---|---|---|---|
| Skin Texture | 3.67 | 5.56 | 1.89 | 51% |
| Wrinkles (Eye area) | 2.89 | 4.33 | 1.44 | 50% |
| Wrinkles (Mouth area) | 2.89 | 3.67 | 0.78 | 27% |
| Wrinkles Neck area | 3.00 | 3.89 | 0.89 | 30% |
| Wrinkle (Forehead) | 3.56 | 4.67 | 1.11 | 31% |
| Skin Elasticity (Sagging) | 3.00 | 4.67 | 1.67 | 56% |
| Skin Tone (Firmness) | 3.11 | 4.78 | 1.67 | 54% |
| Skin Softness | 3.56 | 5.56 | 2.00 | 56% |
| Skin Smoothness | 3.33 | 5.56 | 2.23 | 67% |
| Skin Vibrance | 2.78 | 4.89 | 2.11 | 76% |
| Skin Young Looking | 3.00 | 5.33 | 2.33 | 78% |
| Pore Size | 2.67 | 4.56 | 1.89 | 71% |

TABLE 6

Percentage Improvement of Physical/Mental Condition after taking Lotus (Methyltransferase) Daily Nutrient Tablets (60 days)

| Physical/Mental Condition | Average Score Before Treatment | Average Score After Treatment | Improvement | Increased % |
|---|---|---|---|---|
| Energy | 3.22 | 4.67 | 1.45 | 45% |
| Vitality | 3.11 | 4.56 | 1.45 | 47% |
| Ability to Sleep | 2.89 | 4.11 | 1.22 | 42% |
| General Well Being | 4.22 | 5.44 | 1.22 | 29% |
| Overall Good Health | 4.78 | 5.56 | 0.78 | 16% |
| Mental Performance | 5.11 | 5.89 | 0.78 | 15% |
| Vision | 4.00 | 4.78 | 0.78 | 20% |
| Growth of Hair and Nails | 3.33 | 5.67 | 2.34 | 70% |
| Increased Stamina | 3.44 | 4.89 | 1.45 | 42% |
| Feeling Younger | 3.11 | 4.89 | 1.78 | 57% |

I claim:

1. An oral composition for the treatment of age-related damage to the skin and for improvement of vitality level comprising:
   (a) an effective amount of an extract of the whole flower of Lotus; and
   (b) a compatible carrier.

2. The oral composition of claim 1 wherein said extract of the whole flower of Lotus is an extract from one of the species of Lotus selected from the group consisting of Sacred Lotus, Egyptian Lotus, Yellow Lotus, Red Lotus, Purple Lotus, Pink Lotus, White Lotus, Blue Lotus, Orange Lotus and Golden Lotus.

3. The oral composition of claim 1, wherein said extract of the whole flower of Lotus is present in an amount of from about 0.01% to about 99.9% by weight.

4. The oral composition of claim 1 wherein said oral composition is selected from the group consisting of liquid, gel, powder, tablet, caplet, capsule and soft gel.

5. The oral composition of claim 1 wherein said oral composition further comprises an antioxidant.

6. The oral composition of claim 1, wherein said oral composition further includes vitamins.

7. The oral composition of claim 1, wherein said oral composition further includes minerals.

8. The oral composition of claim 1, wherein said oral composition further includes methyl donors.

9. The oral composition of claim 8, wherein said methyl donor is S-adenosylmethionine.

10. The oral composition of claim 1, wherein said oral composition further includes growth hormone agonists.

11. An oral composition for the treatment of age-related damage to the skin and for improvement of vitality level comprising:
   (a) an effective amount of an extract of the whole see of Lotus; and
   (b) a compatible carrier.

12. The oral composition of claim 11 wherein said extract of the whole seed of Lotus is an extract from one of the species of Lotus selected from the group consisting of Sacred Lotus, Egyptian Lotus, Yellow Lotus, Red Lotus, Purple Lotus, Pink Lotus, White Lotus, Blue Lotus, Orange Lotus and Golden Lotus.

13. The oral composition of claim 11 wherein said extract of the whole seed of Lotus is present in an amount of from about 0.01% to about 99.9% by weight.

14. The oral composition of claim 11, wherein said oral composition is selected from the group consisting of liquid, gel, powder, tablet, caplet, capsule and soft gel.

15. The oral composition of claim 11 wherein said oral composition further comprises an antioxidant.

16. The oral composition of said oral composition further includes vitamins.

17. The oral composition of claim 11, wherein said oral composition further includes minerals.

18. The oral composition of claim 11, wherein said oral composition further includes methyl donors.

19. The oral composition of claim 18, wherein said methyl donor is S-adenosylmethionine.

20. The oral composition of claim 11, wherein said oral composition further includes growth hormone agonists.

* * * * *